(12) United States Patent
Maiser et al.

(10) Patent No.: US 10,696,940 B2
(45) Date of Patent: Jun. 30, 2020

(54) MODULAR SYSTEM AND PROCESS FOR THE CONTINUOUS, MICROBE-REDUCED PRODUCTION AND/OR PROCESSING OF A PRODUCT

(71) Applicant: BAYER AKTIENGESELLSCHAFT, Leverkusen (DE)

(72) Inventors: Benjamin Maiser, Leverkusen (DE); Peter Schwan, Leverkusen (DE); Martin Lobedann, Köln (DE); Volker Möhrle, Köln (DE)

(73) Assignee: BAYER AKTIENGESELLSCHAFT, Leverkusen (DE)

(*) Notice: Subject to any disclaimer, the term of this patent is extended or adjusted under 35 U.S.C. 154(b) by 231 days.

(21) Appl. No.: 15/571,754

(22) PCT Filed: Apr. 29, 2016

(86) PCT No.: PCT/EP2016/059700
§ 371 (c)(1),
(2) Date: Nov. 3, 2017

(87) PCT Pub. No.: WO2016/177650
PCT Pub. Date: Nov. 10, 2016

(65) Prior Publication Data
US 2018/0135006 A1    May 17, 2018

(30) Foreign Application Priority Data
May 7, 2015   (EP) .................................. 15166686

(51) Int. Cl.
*B01D 15/18*   (2006.01)
*B01D 19/00*   (2006.01)
(Continued)

(52) U.S. Cl.
CPC ......... *C12M 47/12* (2013.01); *B01D 15/1864* (2013.01); *B01D 19/0031* (2013.01);
(Continued)

(58) Field of Classification Search
None
See application file for complete search history.

(56) References Cited

U.S. PATENT DOCUMENTS

| 6,773,613 B1 * | 8/2004 | Winslow ............. A61M 1/3693 |
| | | 210/739 |
| 2002/0095028 A1 * | 7/2002 | Grimes ................ B01D 61/145 |
| | | 530/412 |

(Continued)

FOREIGN PATENT DOCUMENTS

| EP | 0249932 A2 | 12/1987 |
| EP | 2182990 A1 | 5/2010 |

(Continued)

OTHER PUBLICATIONS

International Search Report of International Patent Application No. PCT/EP2016/059700 dated Jul. 22, 2016.

*Primary Examiner* — Bradley R Spies
(74) *Attorney, Agent, or Firm* — McBee Moore & Vanik IP, LLC (57) ABSTRACT

The invention provides a method for the continuous, microbe-reduced production and/or processing of a biopharmaceutical, biological macromolecular product from a heterogeneous cell culture-fluid mixture, comprising the steps of: (a) providing a particle-free fluid from a heterogeneous cell culture-fluid mixture containing the product, in the form of a product stream, (b) at least one filtration, providing a filtrate, (c) at least two chromatography steps for purifying the product, (d) at least one virus depletion, (e) at least one ultrafiltration and/or at least one diafiltration of the product stream of steps (b), (c) and/or (d), characterized in that the (Continued)

at least two chromatography steps from (c) comprise a purification via at least two chromatography columns and/or membrane adsorbers in each case and that the process is carried out in a closed and modular manner The invention further provides a corresponding modular system for carrying out said method.

1 Claim, 4 Drawing Sheets (51) Int. Cl.
    *B01D 61/24*     (2006.01)
    *B01D 61/58*     (2006.01)
    *C07K 1/36*     (2006.01)
    *C12M 1/00*     (2006.01)
    *C12M 1/12*     (2006.01)
    *B01D 61/14*     (2006.01)
    *C07K 16/00*     (2006.01)

(52) U.S. Cl.
    CPC ......... *B01D 61/142* (2013.01); *B01D 61/145* (2013.01); *B01D 61/243* (2013.01); *B01D 61/58* (2013.01); *C07K 1/36* (2013.01); *C07K 16/00* (2013.01); *C12M 37/00* (2013.01); *C12M 47/16* (2013.01); *B01D 2311/12* (2013.01); *B01D 2311/2626* (2013.01); *B01D 2311/2649* (2013.01); *B01D 2315/16* (2013.01)

(56) References Cited

U.S. PATENT DOCUMENTS

| | | | |
|---|---|---|---|
| 2006/0246537 A1* | 11/2006 | Jenkins | C12M 23/14 435/68.1 |
| 2009/0084267 A1* | 4/2009 | Furey | B01D 19/0042 96/194 |
| 2012/0199227 A1* | 8/2012 | Manser | A47J 31/0673 137/602 |
| 2013/0112624 A1* | 5/2013 | Gebauer | G01N 30/34 210/656 |
| 2013/0344535 A1* | 12/2013 | Mundt | C12N 5/0602 435/41 |
| 2014/0255994 A1 | 9/2014 | Konstantinov et al. | |
| 2014/0284271 A1* | 9/2014 | Kassebaum | C02F 3/322 210/602 |
| 2015/0133636 A1* | 5/2015 | Xenopoulos | B01D 15/362 530/387.1 |
| 2015/0133642 A1* | 5/2015 | Hekmat | B01D 9/005 530/388.1 |
| 2016/0083454 A1* | 3/2016 | Duthe | C07K 1/16 530/388.26 |

FOREIGN PATENT DOCUMENTS

| | | | | |
|---|---|---|---|---|
| EP | 2682168 A1 | 1/2014 | | |
| WO | 2009/032662 A1 | 3/2009 | | |
| WO | 2012/051147 A1 | 4/2012 | | |
| WO | 2012/078677 A2 | 6/2012 | | |
| WO | WO-2013167720 A1 * | 11/2013 | ............ | B01D 9/005 |
| WO | 2014/180852 A1 | 11/2014 | | |

* cited by examiner

MODULAR SYSTEM AND PROCESS FOR THE CONTINUOUS, MICROBE-REDUCED PRODUCTION AND/OR PROCESSING OF A PRODUCT

CROSS-REFERENCE TO RELATED APPLICATIONS

This application is a National Stage entry of International Application No. PCT/EP2016/059700, filed 29 Apr. 2016, which claims priority to European Patent Application No. 15166686.4, filed 7 May 2015.

BACKGROUND

Field

The invention relates to a modular system and a method for the continuous, microbe-reduced production and/or processing of a product from a heterogeneous cell culture-fluid mixture.

Description of Related Art

In biotechnological production, proteins are usually purified in batches. This means that the individual production cycles are handled discontinuously in a batchwise manner, with the entire product being removed after completion of a production cycle. To produce again, it is then necessary to start a separate new product cycle/ batch.

In recent years, it has been increasingly demonstrated that a continuous procedure can also be performed in biotechnological production, where the process runs without interruptions, in contrast to a batch process.

The highly regulated pharmaceutical production requires great effort in terms of time, technology and personnel to provide cleaned and sterilized bioreactors and to ensure a sterile product. To reliably avoid cross-contamination in the event of a product changeover in a multipurpose system or between two product batches, what is required apart from cleaning is a very complex cleaning validation, which, if applicable, must be repeated in the event of a process adaptation.

This applies both to upstream processing (USP), i.e. the production of biological products in fermenters, and to downstream processing (DSP), i.e. the purification of the fermentation products.

Especially in the case of fermentation, a sterile environment is essential for a successful culture.

To sterilize batch fermenters or fed-batch fermenters, the SIP technique (SIP=sterilization-in-place) is generally used.

The downtime of reactors resulting from the necessary cleaning and sterilization procedures can take up a significant share of reactor availability, especially in the case of short usage periods and frequent product changes. This affects, for example, the process steps of media preparation and fermentation in USP of biotechnological production, and solubilization, freezing, thawing, pH adjustment, production separation, e.g. via chromatography, precipitation or crystallization, adjusting buffers and virus inactivation in DSP.

In the downstream process, the regulatory requirements are a microbe-reduced process management. Therefore, there is no need for a sterile process in the case of batch operation.

However, in a continuous process, the purification of the protein is performed over a relatively long period of time if possible without cleaning steps. This preferably occurs without sterilization steps during the purification. This is the case even though the risk of microbial contamination is many times higher than in the case of a simple batch operation.

WO2012/078677 describes a process and a system for the continuous processing of biopharmaceutical products by means of chromatography and the integration thereof in a production system, more particularly in a disposable system. Although WO2012/078677 provides approaches for the continuous production of biopharmaceutical and biological products, the disclosed solution is not adequate in practice. WO2012/078677 also does not disclose the use of a sterilized chromatography column.

US 2014/0255994 A1 discloses an integrated continuous process for producing therapeutic proteins. However, US 2014/0255994 A1 does not disclose the feature that sterilized chromatography columns could be used in such a process.

EP 2 182 990 A1 discloses a process for sterilizing chromatography columns by using hot water vapour.

First of all, some terms will be defined in more detail.

In the context of this invention, a continuous process means any process for carrying out at least two process steps in series, the output stream of an upstream step being conveyed to a downstream step in said process. The downstream step starts the processing of the product stream before the upstream step has been completed. Typically, in a continuous process, part of the product stream is always being conveyed in the production system and is referred to as a "continuous product stream". Accordingly, a continuous conveyance or transfer of a product stream from an upstream unit to a downstream unit means that the downstream unit is already operating before the upstream unit is put out of operation, i.e. that two successively connected units simultaneously process the product stream flowing through them.

In the context of the invention, the term "microbe-reduced" means a state of reduced microbial count, i.e. a microorganism count per unit area or unit volume of virtually zero, which is achievable by a suitable microbe-reduction method, it being possible to select said microbe-reduction method from gamma irradiation, beta irradiation, autoclaving, ethylene oxide (ETO) treatment and "steam-in-place" (SIP) treatment.

In the context of the invention, the term "disposable article" means that the articles in question that come into contact with product, more particularly apparatuses, tanks, filters and connecting elements, are suitable for one-time use with subsequent disposal, it being possible for said tanks to be made both from plastic and from metal. In the context of the invention, the term also encompasses reusable articles, for instance made of which are used only once in the process according to the invention and are then no longer used in the process. In the context of the invention, said reusable articles, made of steel for example, are then also referred to as "objects used as disposable articles". Such employed disposable articles can also be referred to as "disposable" or "single-use" articles ("SU technology"), respectively, in the process according to the invention. These yet further improve the microbe-reduced state of the process according to the invention and of the modular system.

In the context of the invention, the term "product stream" means the particle-free fluid from a heterogeneous cell culture/fluid mixture containing the product, and the result of each of the other process steps of the process according to the invention, i.e. the product stream after filtration, after chromatography, after virus depletion, after ultrafiltration, after diafiltration, or after further steps of the process according to the invention, it then being possible for said product streams to have different concentrations and degrees of purity.

In the context of the invention, the term "virus depletion" means a reduction in the concentration of active viruses per unit volume of the fluid to be treated, right up to complete inactivation and/or removal of the viruses present in the fluid to be treated.

In the context of the invention, the term "microbicide" means a substance which can slow or completely inhibit the growth of microorganisms, it being possible for said microbicide to be used in the form of a microbicide-containing buffer, especially during an ultrafiltration in the context of the process according to the invention.

In the context of the invention, the term "bubble trap" means a device for collecting gas bubbles while the fluid in question is degassed at the same time, with the fluid in question being degassed when this is taking place.

In the context of the invention, the term "modular" means that the individual steps of the process according to the invention can be carried out in separate modules that are connected to one another, the modules being preconfigured and microbe-reduced and it being possible to connect them to one another in a closed manner and in different combinations.

In the context of the invention, the term "modular system" means a series of modules ("units") in which a fluid ("product stream") can be conveyed and which are connected to one another for carrying out at least two downstream and/or upstream steps. According to the invention, the units are suitable for continuously carrying out a step and can be operated with a continuous fluid stream ("product stream"). In this connection, the individual modules of the "modular system" can be connected to one another in any combination. Examples of modules in the context of the invention are the filtration module 2, the chromatography module 3, the ultrafiltration module 6, the diafiltration module 7 and the dialysis module 8.

In the context of the invention, the term "closed" means the mode of operation of the process according to the invention and of the modular system according to the invention, which are operated such that the product produced and/or processed by said process and said modular system is not exposed to the room environment. Materials, objects, buffers and the like can be added from the outside to the closed process according to the invention and the corresponding closed modular system according to the invention, however, this addition takes place in such a way that an exposure of the produced and/or processed product to the room environment is avoided.

The processes known from the prior art have a range of disadvantages, which will be dealt with below.

Known processes for producing biopharmaceutical and biological products typically comprise the following production steps, which are connected to one another:
1. perfusion culture
2. cell retention system, as an alternative to steps 1 and 2, also a feed-batch culture may be employed,
3. cell removal
4. buffer or media exchange, preferably with concentration
5. bioburden reduction, preferably by sterile filtration
6. capture chromatography.

Typically, further steps are carried out for further purification of the product stream, more particularly:
7. virus inactivation
8. neutralization, and
9. optionally a further depth filtration, bioburden reduction (sterile filtration).

In view of the high quality standards in the production of biopharmaceuticals, the following steps are typically additionally carried out:
10. chromatographic intermediate and high-quality purification
11. bioburden reduction, for example sterile filtration
12. virus filtration
13. buffer exchange and preferably concentration, and
14. sterile filtration.

In the above-described production, cells in a fermenter containing nutrient solution produce a biological product, for instance a protein, for example a therapeutic protein. The nutrient solution is also an ideal growth medium for microorganisms, such as bacteria and spores. As this growth of such microorganisms is not desired a problem arises from these circumstances. Said undesired growth of microorganisms especially becomes a problem in the case of relatively long run times because the nutrient solution becomes increasingly contaminated as the run time of the process increases, right up to an exponential growth of microorganisms and thus a total loss of the batch of the biological product that is produced.

To cope with the demand for a rapid and flexible reloading of the production system while maintaining maximum cleanliness and sterility, concepts for a continuous production, preferably using disposable technology, are attracting a constantly growing interest in the market.

For relatively long run times of such a process, ranging from two or more hours over days to weeks, customary sanitization measures are, however, insufficient, for example the customary "clean-in-place" (CIP) measures, such as sanitization by means of 1 M NaOH for example. In the case of run times above two or more hours, such customary processes and systems therefore have the disadvantage that they are highly susceptible to possible contamination and/or possible microbial growth.

Therefore, there is a need for a process for the continuous purification of a product from a heterogeneous cell culture-fluid mixture, which due to its microbe-reduced state allows a continuous mode of operation for several weeks.

SUMMARY

It is therefore an object of the present invention to develop a process and a corresponding system, by means of which a product, for instance a protein, can be continuously purified over a period of several hours up to several weeks.

The invention achieves this object by providing a method (process) for the continuous, microbe-reduced production and/or processing of a biopharmaceutical, biological macromolecular product from a heterogeneous cell culture-fluid mixture, comprising the steps of:
(a) providing a particle-free fluid from a heterogeneous cell culture-fluid mixture containing the product, in the form of a product stream,
(b) at least one filtration, providing a filtrate,
(c) at least two chromatography steps for purifying the product,
(d) at least one virus depletion,
(e) at least one ultrafiltration and/or at least one diafiltration of the product stream of steps (b), (c) and/or (d), characterized in that the at least two chromatography steps from (c) comprise a purification via at least two chromatography columns and/or membrane adsorbers in each case and that the method is carried out in a closed and modular manner

DETAILED DESCRIPTION OF A PREFERRED EMBODIMENT

The basis of the method according to the invention are its four core principles and hence core features:
1. continuous
2. microbe-reduced
3. closed, and
4. modular production of a biopharmaceutical, biological macromolecular product.

These four features together drastically reduce the usually occurring problem of the undesired growth of microorganisms, allowing run times of the process according to the invention in a continuous mode of operation of up to 8 weeks.

The particle-free fluid provided in step a) from a heterogeneous cell culture-fluid mixture may preferably originate from a continuous perfusion and fermentation process, for instance a cell culture or tissue culture, or a perfusion reactor. It is even possible for more than one perfusion reactor to be operated in parallel, for instance two perfusion reactors. The fluid can firstly be continuously discharged through suitable cell retention systems, for instance an inclined plates separator (settler), by means of which the majority of cells can be retained. Particles present in the fluid can then be removed from the fluid by subsequent filtration and/or centrifugation steps or other suitable separation methods, yielding a particle-free fluid containing the biopharmaceutical, biological macromolecular product.

The filtration step (b) can, for example, be a filtration of the particle-free fluid obtained after step (a), yielding a filtrate. However, the process according to the invention can also comprise further filtration steps at suitable points in the process.

The filtration step b) can be achieved by suitable filter methods, for example a 0.2 µm filter, or two or more filters operated in parallel. A suitable filter for the filtration step is, for example, a Sartoguard NF 0.2 µm filter, two or more of which can be operated in parallel.

In a further embodiment of the method according to the invention, the filtration step (b) comprises a depth filter with an additional possibility of depleting contaminants such as DNA, protein A, HCP. These can be depth filters having a sufficient zeta potential (Zetapor 3M, Posidyne, Pall) or depth filters having activated carbon (Millistak Merck Millipore).

The at least two chromatography steps for purifying the product of step c) comprise a purification via at least two chromatography columns and/or membrane adsorbers in each case. In this connection, the chromatography columns and/or membrane adsorbers can exhibit any suitable binding principle, for instance affinity of the product for a ligand, ionic interactions, metal chelate binding, hydrophobic interactions or van der Waals forces. For example, the first chromatography step of the at least two chromatography steps can be an affinity chromatography (e.g. a ligand with affinity for the product, such as, for example, protein A, protein G, protein L, IgM, IgG, and a recombinant protein which is different from protein A, protein G, protein L, IgM, IgG and which has an affinity for the product). This is then followed by a further (second) chromatography step, for instance a chromatography via ionic interactions.

In step c) the method according to the invention is flexible in that it can comprise any suitable chromatography principle in any sequence depending on the degree of product purity and product concentration that are to be achieved.

The technical effect of the use of at least two chromatography steps via at least two chromatography columns and/or membrane adsorbers according to step c) is that an individual chromatography step generally cannot ensure sufficient removal of contaminants such as, for example, host cell impurities, aggregates, DNA, protein A, etc.

In addition, this allows a continuous production in one chromatography step, since at least one chromatography column and/or membrane adsorber can be loaded with unpurified product, whereas at least one other chromatography column and/or membrane adsorber can be regenerated or eluted, making it possible to achieve a continuous and effective mode of operation for the process.

In a further embodiment of the method according to the invention, one or more further steps for adjusting the pH and/or for adjusting the conductivity and/or filtration steps and/or concentration steps and/or a buffer exchange are carried out between the at least two chromatography steps in (c) and/or after the virus inactivation in step (d). This allows a mode of operation for the process that is adaptable to the conditions.

The at least one virus depletion of step d) can especially be carried out by adjusting the pH of the particle-free fluid, preferably to a pH of ≤4.0. Adjustment of the pH of the particle-free fluid to be inactivated to ≤4.0 can, for example, be achieved by adding HCl solution. The addition is typically done ahead of the device for virus depletion. Typically, the pH is adjusted to >4 using a base, for example sodium hydroxide solution (NaOH), in order to end the virus depletion.

However, the at least one virus depletion of step d) can also be carried out by means of a solvent/detergent step, in which a virus depletion is achieved by a solvent/detergent.

In a further embodiment, the virus depletion can also be achieved by UV treatment and/or by thermal treatment.

The at least one virus depletion of step d) can take place especially in a residence section, into which a segmented product stream can be introduced.

In a further embodiment of the method according to the invention, all the elements used in steps (a) to (e) that come into contact with the product are subjected to microbe reduction by means of a suitable microbe-reduction method.

Preferably, the microbe-reduction method can be selected from the group consisting of gamma irradiation, beta irradiation, autoclaving, ethylene oxide (ETO) treatment, ozone treatment ($O_3$), hydrogen peroxide treatment ($H_2O_2$) and steam-in-place (SIP) treatment.

Accordingly, the objects and elements of the modules used in the process according to the invention which come into contact with the product stream can preferably be subjected to microbe reduction and/or can be sterilized, preferably can be autoclaved, can be gamma-irradiated, can be flushed with ethylene oxide (ETO), can be treated with ozone ($O_3$), can be treated with hydrogen peroxide ($H_2O_2$) or can be treated with a steam-in-place (SIP) treatment, allowing a microbe-reduced or even aseptic operation of the process according to the invention.

In a further embodiment of the method according to the invention, all elements used from filtration step (b) onwards that come into contact with the product are disposable articles or are used as disposable articles. Such disposable articles can then also be referred to as "single-use" articles ("SU technology") in the process according to the invention. This improves the microbe-reduced state of the process.

In a further embodiment of the method according to the invention, all inlet fluids are filtered through a microbe-reduction filter, such as, for instance, a Sartoguard NF filter from Sartorius.

In this connection, all outlets may preferably be protected by a microbe barrier preventing a back-growth of microorganisms. For example, it is also possible here to use a Sartoguard NF filter from Sartorius as the microbe barrier. An additional reliability of the microbe barrier 11 can be achieved by a changeover switching of filters and/or a waste line. A further measure to ensure the microbe-reduced conditions can be achieved by a periodic sanitization of the waste line, preferably after filtration, with NaOH solution for example. Further possible methods are UV irradiation and heat treatment.

In a further embodiment, the modular process steps of the method according to the invention are preferably carried out in modules, the modules being connected to one another. Preferably, the modules may be connected to one another by welding or by aseptic connectors. To weld the modules, for example, the "TC Welder" instrument from Sartorius can be used.

In a further embodiment of the method according to the invention, all the used liquids, gases and solids are subjected to microbe reduction in steps (a) to (e). In this connection, the microbe reduction is preferably achieved by means of a filtration through a filter having a pore size of preferably ≤0.45 µm. In this case, in-process sterilization is preferably not carried out during the process. In other embodiments, it is also possible to carry out the microbe reduction by means of a filtration through a filter having a pore size of preferably ≤0.20 µm.

In a further preferred embodiment of the method according to the invention, a degassing of all fluids which come onto the at least two chromatography columns is carried out before chromatography step (c), the degassing preferably being achieved by means of at least one bubble trap and/or by means of at least one hydrophobic microfiltration membrane via vacuum and/or by treatment with ultrasound and/or by sparging with a poorly soluble gas, such as helium for example.

In this connection, the use of a hydrophobic microfiltration membrane via vacuum is preferred for maintaining sterility in the continuous conduct of the process according to the invention and of the system according to the invention, since this has been found to be especially advantageous in comparison with the bubble trap. The used hydrophobic microfiltration membrane can be in particular a MicroModule from Membrana.

In an especially preferred embodiment of the method according to the invention, the particle-free fluid from step a) is subjected to at least one ultrafiltration against a microbicide-containing buffer. As a result of the ultrafiltration, the nutrients present in the fluid are replaced with a microbicide-containing buffer in order to deprive microorganisms/microbes of the conditions for growth in the fluid. This additionally improves the microbe reduction of the process.

The microbicide used in this connection, or one or more microbicides, may preferably be selected from the group consisting of imidazole, benzoic acid, sorbic acid, para-hydroxybenzoic esters, sulphites, disulphites, azides, ortho-phenylphenol, nisin, natamycin, hexamethylenetetramine, dimethyl dicarbonate, nitrites, nitrates, acetic acid, ascorbic acid, isoascorbic acid, L-lactic acid, propionic acid, boric acid and lysozyme.

The microbicides present in the microbicide-containing buffer can furthermore be one or more microbicides from the group consisting of:
E210 to E213: Benzoic acid and the salts thereof, 0.05-0.1% in solvent in acidic environment, 2-3 g/kg in solvent;
E200 to E203: Sorbic acid and the salts thereof, 300-2000 mg/kg;
E214 to E219: PHB esters (para-hydroxybenzoic esters, parabens), butylparaben and propylparaben;
E220 to E228: Sulphites and disulphites;
E231 and E232: Ortho-phenylphenol, 12 mg/kg;
E234: Nisin;
E235: Natamycin;
E239: Hexamethylenetetramine, 25 mg/kg;
E242: Dimethyl dicarbonate;
E249-E252: Nitrites and nitrates, 300 mg/kg;
E260: Acetic acid, 0.5-3%;
E300-E302: Ascorbic acid, 300 mg/kg;
E315-E316: Isoascorbic acid, 1500 mg/kg;
E261-E263: Acetate;
E270: L-Lactic acid;
E280 to E283: Propionic acid and the salts thereof, 1-3 g/kg;
E284 and E285: Boric acid, max. 4 g/kg;
E1105: Lysozyme; and Azides.

In a preferred embodiment of the method according to the invention, the biopharmaceutical, biological macromolecular product is a protein or peptide selected from the group consisting of monoclonal antibodies, polyclonal antibodies, recombinant proteins and vaccines, preferably DNA and RNA vaccines.

The chromatography columns and/or membrane adsorbers used in step c) can exhibit any suitable binding principle, for instance affinity of the product for a ligand, ionic interactions, metal chelate binding, hydrophobic interactions or pure van der Waals forces. For example, the first chromatography step of the at least two chromatography steps can be an affinity chromatography (e.g. a ligand with affinity for the product, such as, for example, protein A, protein G, protein L, IgM, IgG and a recombinant protein which is different from protein A, protein G, protein L, IgM, IgG and which has an affinity for the product). This is then followed by a further (second) chromatography step, for instance a chromatography via ionic interactions.

At this stage the method according to the invention is flexible. It can comprise in step c), any suitable chromatography principle in any sequence depending on the degree of product purity and product concentration that are to be achieved.

In a particularly preferred embodiment of the method according to the invention, the at least two chromatography columns and/or membrane adsorbers of step (c) comprise a ligand preferably selected from the group consisting of protein A, protein G, protein L, IgM, IgG and a recombinant protein which is different from protein A, protein G, protein L, IgM and IgG and which has an affinity for the product.

In a preferred embodiment of the method according to the invention, the process of steps (a) to (e) has a run time of at least 4 hours, preferably of at least 8 hours, preferably of at least 12 hours, preferably of at least 24 hours, more preferably of at least 48 hours, more preferably of at least 7 days, more preferably of at least 4 weeks, and particularly preferably of at least 8 weeks. Such a long run time of two or more weeks of continuous operation is only feasible with the closed, modular and, especially, microbe-reduced mode of operation of the process.

In a preferred embodiment of the method according to the invention, at least one filtration step comprising at least one filter is carried out between steps a) to e) and/or thereafter.

In a particularly preferred embodiment of the method according to the invention, the filter is automatically changed under microbe-reduced conditions, the automatic filter change preferably comprising the following steps:
(i) switching of the flow path to a new filter in the event of exceeding of a threshold at the pressure sensor on the non-filtrate side with closing of the flow path, the product in the used filter preferably being pushed into the filtrate side by a gas or a liquid,
or in the event of exceeding of a maximum time of the used filter in the flow path, or in the event of exceeding of a maximum volume of filtrate through the used filter,
(ii) venting of the new filter via an air filter having a pore size of preferably <=0.25 µm at the venting valve of the new filter, preferably with conveyance of product into the new filter by means of a feed pump, or into a closed bag connected in a microbe-reduced manner,
(iii) detecting the completion of venting of the new filter on the non-filtrate side by means of the pressure sensor or a fill-level sensor or a balance or a liquid detector,
(iv) opening the filtrate outlet and closing the flow path between the venting valve and the air filter by means of a valve, and
(v) exchanging the old filter for a new filter.

The simultaneous or downstream transportation of product into the new filter can, for example, be achieved by means of a feed pump.

This means that, in a further embodiment of the method according to the invention, the filter change (switching from a used filter element to a new one) can be done automatically. What is found to be problematic here is the filter venting, which, however, is necessary and which must be carried out manually in the case of the filters currently available. Firstly, the filter is subjected to a microbe-reduction method by means of, appropriate.g., ETO, autoclaving or gamma irradiation and then joined to the process. Thereafter, the filter can be filled on the non-filtrate side while the venting valve is open. This valve must be closed after successful venting so that the actual filtration can be carried out. In a batch process, a strict microbe-reduced handling on the non-filtrate side is not necessary. This is the case as a batch process only runs for a short period of time. Thus, it is merely important to obtain a filtrate which is as microbe reduced as possible., In a continuous process, however, the strict microbe-free operation of the non-filtrate side is also required in order to prevent a microbial contamination of the process. In the prior art, the venting valve must be closed manually after filling of the filter by means of a rotational movement so that the actual filtration can be carried out. Said rotational movement it difficult to automate asit also needs an axial movement of the rotational body. As a result of the axial movement of the rotational body together with the seals applied thereon, the boundary is shifted. If prior to said manual closing of the venting valve a microbe reduction was carried out while the venting valve was closedthe microbe boundary is shifted upon opening of the venting valve. This introduces a microbe-containing area into the microbe-reduced area, and thus nullifies the microbe reduction. A microbe reduction with an opened filter valve is not recommended, since the open position does not have a fixed position, and damage to the valve can occur easily. In addition, the open position is usually wobbly, and hence shifting of the microbe boundary can occur through the normal handling of the filter.

In the case of automatic filter venting, it is advantageous to avoid the rotational movement of the venting valve during initial operation so that the venting can be carried out merely by simple measures. The venting valve can then be modified such that it is permeable even in the closed state, but continues to reliably seal off the environment. As a result, the valve is "closed" in the safe state, and this is characterized by a tight fit. The "open" state is usually not clearly defined, since the valve body greatly wobbles during operation and allows a shifting of the boundary. A length of tubing which ends in a hydrophobic <=0.2 µm air filter is attached to the nozzle of the rotational body. This arrangement is then preferably subjected to microbe reduction by ETO, gamma irradiation, autoclaving, or ozone ($O_3$) treatment or by hydrogen peroxide ($H_2O_2$) treatment. Therefore, the entire non-filtrate side up to the air filter on the venting valve is microbe-reduced or low-microbe. Between the venting valve and the air filter, the length of tubing is inserted into a tubing pinch valve capable of reliably pinching the length of tubing. In this way, venting can be achieved in a fully automatic and low-microbe manner. The filter is filled until liquid enters the air filter by means of the venting valve and the length of tubing. The hydrophobic venting filter blocks the liquid. At the same time, the process system blocks the production stream by means of a valve on the filtrate side, and so there is a pressure rise in front of the filter. Said pressure rise is detected by means of a suitable sensor. If a certain threshold pressure is exceeded, the pinch valve of the venting tubing is closed, and the valve on the filtrate side is opened. Via this procedure, it is possible to modify the filter automatically without manual intervention using a modified venting valve.

Figure 2:
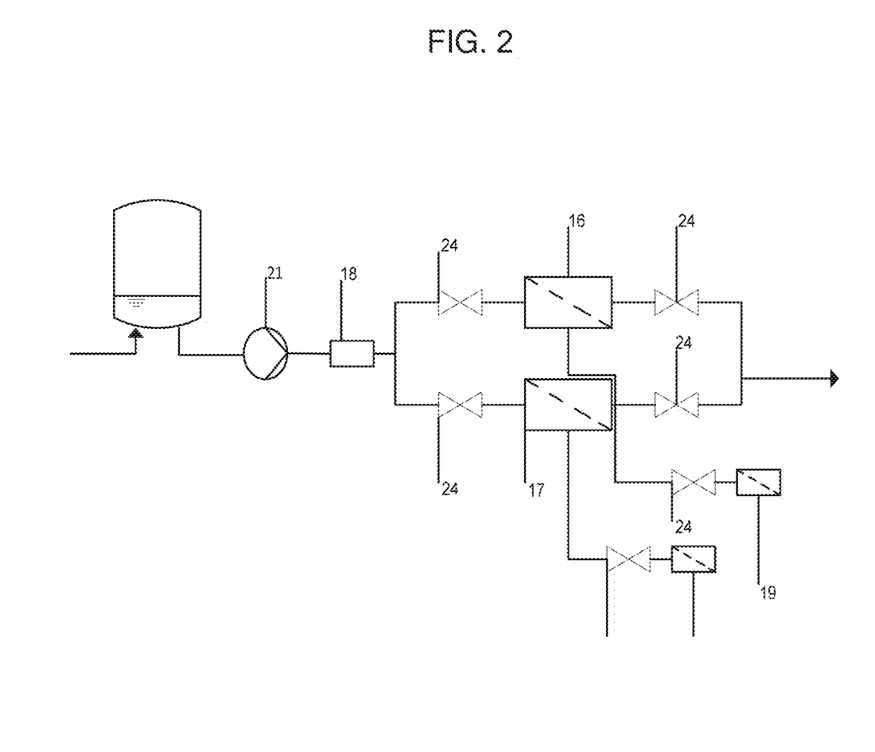
FIG. 2 shows schematically the operating principle of the filtration step of the process and of the system with replacement of a used filter 17 by welding-in of a new filter 16.

This automatic filter change is shown by way of example in FIG. 2, which illustrates schematically the operating principle of the filtration step of the process and of the system with replacement of a used filter 17 by welding-in of a new filter 16.

At the end of the process, the final purified biopharmaceutical, biological macromolecular product from the heterogeneous cell culture-fluid mixture can be filtered one last time by a final filtration, preferably through a filter having a pore size of 0.2 µm. The final filtration can, for example, be achieved across gamma-irradiated Sartopore 2 capsules (Midicap size 7, 0.05 $m^2$) into a gamma-irradiated 5 litre GE ReadCircuit bag. When the fill level of the final bag is acceptable, said bag can then be welded off and a new bag can be welded to the process.

The invention further achieves said object by providing a modular system for the continuous, microbe-reduced production and/or processing of a biopharmaceutical, biological macromolecular product from a heterogeneous cell culture-fluid mixture, comprising the following modules:
(a) at least one filtration module,
(b) at least one chromatography module, comprising at least two chromatography columns and/or membrane adsorbers,
(c) at least one ultrafiltration module and/or at least one diafiltration module and/or at least one dialysis module, and
(d) at least one module for continuous virus depletion, characterized in that the modular system is closed and microbe-reduced.

However, the at least one chromatography module can also comprise more than two chromatography columns and/or membrane adsorbers, for example three or four chromatography columns and/or membrane adsorbers.

In a further embodiment of the modular system according to the invention, all the elements that come into contact with product and are used in modules (a) to (d) are subjected to microbe reduction by means of a microbe-reduction method, the microbe-reduction method preferably being selected from the group consisting of gamma irradiation, beta irradiation, autoclaving, ethylene oxide (ETO) treatment, ozone treatment ($O_3$), hydrogen peroxide treatment ($H_2O_2$) and steam-in-place (SIP) treatment.

Preferably, the modular system itself, and also the elements of the modules that come into contact with product stream, can be subjected to microbe reduction and/or can be sterilized, preferably can be autoclaved, can be gamma-irradiated, can be flushed with ethylene oxide (ETO), can be treated with ozone ($O_3$), can be treated with hydrogen peroxide ($H_2O_2$) or can be treated with a steam-in-place (SIP) treatment, allowing a low-microbe or even aseptic operation of the modular system according to the invention.

In a further embodiment of the modular system according to the invention, all objects used in modules (a) to (d) that come into contact with the product are disposable articles or are used as disposable articles. In this connection, the modules are preferably connected to one another by welding or by aseptic connectors. For example, aseptic "ReadyMate" connectors from GE are aseptic connectors preferably used in the modular system according to the invention.

Preferably, ready-to-use disposable articles are used as gamma-irradiated elements.

In a preferred embodiment of the modular system according to the invention, all inlet fluids pass through a microbe-reduction filter, with all outlets preferably being protected by a microbe barrier preventing a back-growth.

At the end of the modular system, the final purified biopharmaceutical, biological macromolecular product from the heterogeneous cell culture-fluid mixture can be filtered one last time by a final filtration, preferably through a filter having a pore size of 0.2 μm. The final filtration can, for example, be achieved across gamma-irradiated Sartopore 2 capsules (Midicap size 7, 0.05 $m^2$) into a gamma-irradiated 5 litre GE ReadCircuit bag. When the fill level of the final bag is acceptable, said bag can then be welded off and a new bag can be welded to the process.

The present invention including preferred embodiments will be explained in more detail in the following drawings and the example without being restricted thereto. The embodiments can be combined with one another as desired, if the contrary is not clearly evident from the context.

The following are shown.

Figure 4:
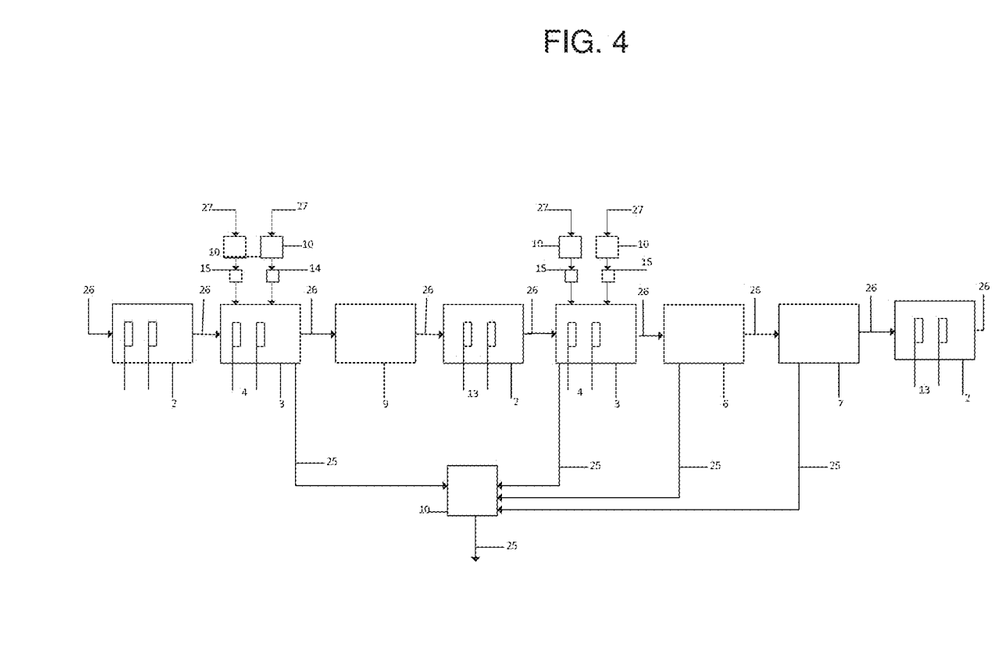
FIG. 4 shows exemplarily the modular structure of the system, with all inlet streams and outlet streams being connected to the environment via a microbe barrier 10, 13.

The exemplary modular system 1 consists of three filtration modules 2 each having two filters 13, which are operated alternatively, two chromatography modules 3 having two chromatography columns 4 or two membrane adsorbers 5, a virus depletion step, for example virus inactivation 9, an ultrafiltration module 6 and a diafiltration module 7. Gas bubbles are removed from the buffers via a hydrophobic filter 15 or bubble trap 14.

Figure 1:
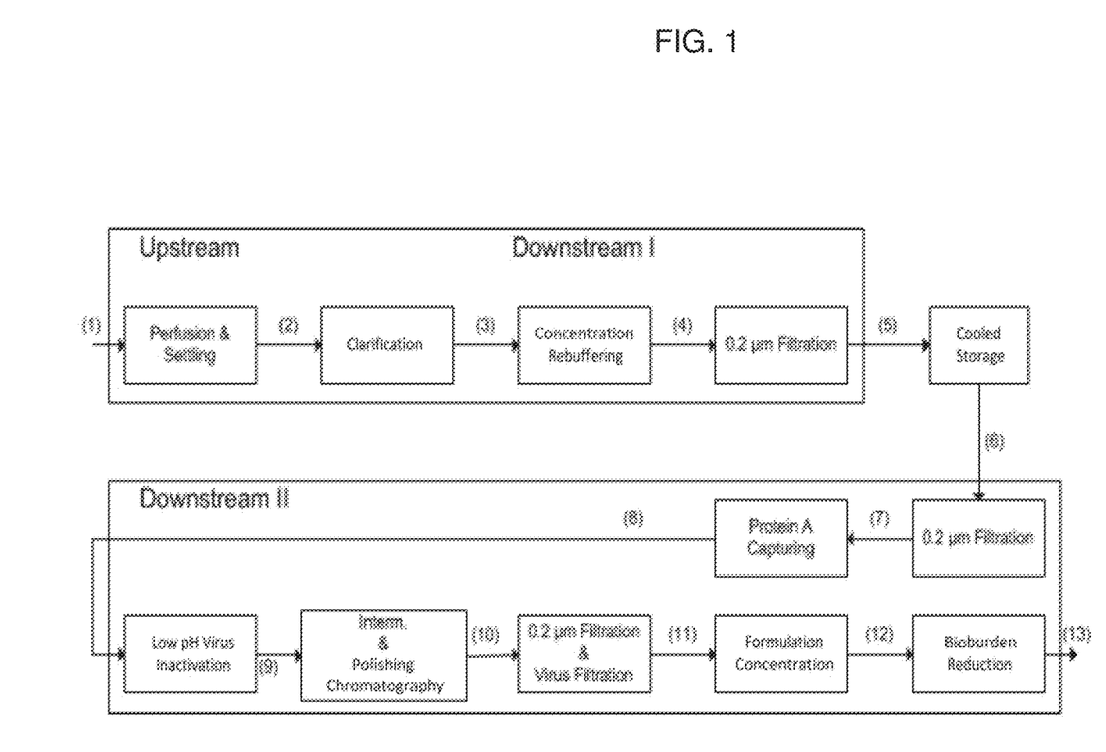
FIG. 1 shows schematically a process diagram of one embodiment of the process according to the invention. The numbers between parentheses are references to the mass balance, as listed in Example 1 and Table 1.

Table 1 shows the averaged flow rates and antibody concentrations of the positions shown in FIG. 1.

The reference numerals used are:
1=Modular system
2=Filtration module
3=Chromatography module
4=Chromatography column
5=Membrane adsorber
6=Ultrafiltration module
7=Diafiltration module
8=Dialysis module
9=Virus depletion
10=Microbe-reduction filter
11=Microbe barrier
12=Aseptic connector
13=Filter having a pore size of preferably ≤0.45 μm
14=Bubble trap
15=Hydrophobic microfiltration membrane
16=New filter
17=Used filter
18=Pressure sensor
19=Air filter, pore size preferably <=0.25 μm
20=Venting valve of the new filter 16
21=Feed pump
22=Fill level sensor
23=Balance
24=Valve
25=Waste stream
26=Product stream
27=Buffer
28=Liquid detector
29=Bag Example 1

To purify a protein in a continuous and microbe-reduced manner from a heterogeneous cell culture/fluid mixture, a miniplant having the following modules and associated process steps was set up:

Unless otherwise noted, MasterFlex peristaltic pumps having an EasyLoad II pump head were used in the process. The tubing used was Masterflex LS16 or Cflex or Sanipure. All used components coming into contact with product were subjected to 25 kGy gamma irradiation. In exceptional cases where gamma irradiation was not feasible because of the material, components were autoclaved at 121° C. for 20 min, e.g.sub-assemblies having pH probes or virus filters. Where possible, ready-to-use disposable articles were used as gamma-irradiated modules. Without exception, this was the case for all bags. Said bags were generally connected to the modules using ReadyMate® connectors from General Electric (GE). Between each module, a single-use gamma-irradiated bag (ReadyCircuit 1 litre, GE) was placed as compensation tank between the outlet stream of module n-1 and the inlet stream of module n. Generally, there was an inlet stream and an outlet stream at that point in time in each module. Where a venting of the product liquid was advantageous, the tanks were sealed off from the environment via a hydrophobic 0.2 μm filter.

A. Upstream
i) Perfusion Reactor

For the continuous production of an IgG monoclonal antibody, a 10 litre perfusion reactor was used. The viable cell density was 60-70 million cells/ml in the steady state. The titre was ~115 mg/l. Production was carried out for 28 days using two parallel perfusion reactors.

ii) Cell Retention System

The product was continuously discharged across an inclined plates separator (settler), by means of which the majority of cells were retained.

B. Downstream DSP-1
i) Cell Clarification

Clarification was carried out using Sartoguard NF 0.2 µm filters (T-style, MaxiCap, 0.65 m$^2$) operated in parallel. FIG. 2 shows how a closed low-microbe process was realized here. Both the filters and the tubing assembly were gamma-irradiated. The inlet and outlet lines were connected via aseptic connectors to gamma-irradiated bags (GE Ready-Circuit 1 litre), which were used as compensatory volumes for fluctuating flow rates. For the purpose of venting, the filters were coupled to hydrophobic 0.2 µm air filters, and as a result, the module was closed in the meaning of the invention (FIG. 2). The air filter was either an Emflon II from Pall Corp. or a Midisart 2000 from Sartorius Stedim. The venting valves were modified such that they were permeable even in the closed state, but still reliably sealed off the environment. To this end, the inner sealing ring of the venting valve was removed on the Sartoguard NF and the valve was closed prior to gamma irradiation. Said valve was additionally secured against opening. As a result, the valve was "closed" in the safe state, and this was characterized by a tight fit. The venting valve was connected to the air filter via a length of tubing. Between the venting valve and the air filter, the length of tubing was inserted into a tubing pinch valve. The filter was filled until liquid entered the air filter by way of the venting valve and the tubing. The hydrophobic venting filter then blocked the liquid. At the same time, the process system blocked the production stream by ways of a valve on the filtrate side, and so there was a pressure rise in front of the filter. Said pressure rise was detected by means of a Pendotech pressure sensor. If a threshold of 0.5 bar was exceeded, the pinch valve of the length of venting tubing was closed, and the valve on the filtrate side was opened.

ii) Concentration and Rebuffering

The filtrate from the i) cell clarification was firstly continuously concentrated by a factor of 10 using an ultrafiltration hollow-fibre membrane (GE Healthcare ReadytoProcess, 0.2 m$^2$, gamma-irradiated). The circulation pump used was a disposable QuattroFlow 1200 SU pump, the pump head of which was integrated into the tubing assembly prior to gamma irradiation.

The media constituents of the concentrated product were then exchanged for a 50 mM imidazole/NaCl buffer across a Gambro Revaclear 300 dialysis membrane. The module is provided sterile-packed by the manufacturer and was connected to the gamma-irradiated tubing assembly in a biological safety cabinet. The permeate from the concentration and the media-containing waste stream were conducted into a gamma-irradiated 200 litre Sartorius Flexboy. The Flexboy was exchanged by rewelding using a Sartorius welder.

0.2 µm Filtration

Prior to filling, the product was continuously filtered into a 200 litre Flexboy using gamma-irradiated Sartoguard NF filters (MaxiCap size 8) operating alternatively. The setup and operation were similar to "B. Downstream DSP-1-i) Cell clarification".

C. Downstream DSP-II
0.2 µm Filtration

After storage, the product from DSP-1 was filtered again in order to protect the downstream chromatography columns from particles.

1. Capture Chromatography

Mabselect Sure (GE) was used as Prot-A resin to isolate the IgG. The IgG was concentrated by up to a factor of 10 and the majority of the contaminants was removed. A continuous BioSMB system from Tarpon Biosystems, Inc. was used with 12 columns (ID 16 mm, L 80 mm), with 8 columns being in the loading zone (2 columns in series and 4 parallel series). The entire flow path including the columns was rendered microbe-reduced by sanitization or gamma irradiation. The load per cycle was 32 column volumes per column. The buffers used were acetate buffers with differing molarity, pH and conductivities. All buffers were filtered into a gamma-irradiated bag using a gamma-irradiated or autoclaved 0.2 µm filter. The outlet tubing of the buffer bags was welded to the inlets of the BioSMB system. Said system had at each of its inlets a gamma-irradiated degasser membrane (Liquicell Micro Module, Membrana). Similarly, the product line was welded to the inlet of the BioSMB system via such a degasser. All inlet streams were then degassed by means of a vacuum pump at 50 mbar.

1. Virus Inactivation and Neutralization

Virus inactivation and neutralization consisted of three modules and was situated between the capture chromatography and a 0.2 µm filtration: (a) a homogenization loop with a peristaltic pump M0502; (b) a residence-time loop shown schematically as coiled tubing; (c) a neutralization bag in which the pH could be adjusted to 7.5. The modules were individually prefabricated and gamma-irradiated in line with the welding points in FIG. 3, with the ends being welded closed in each case.

Figure 3:
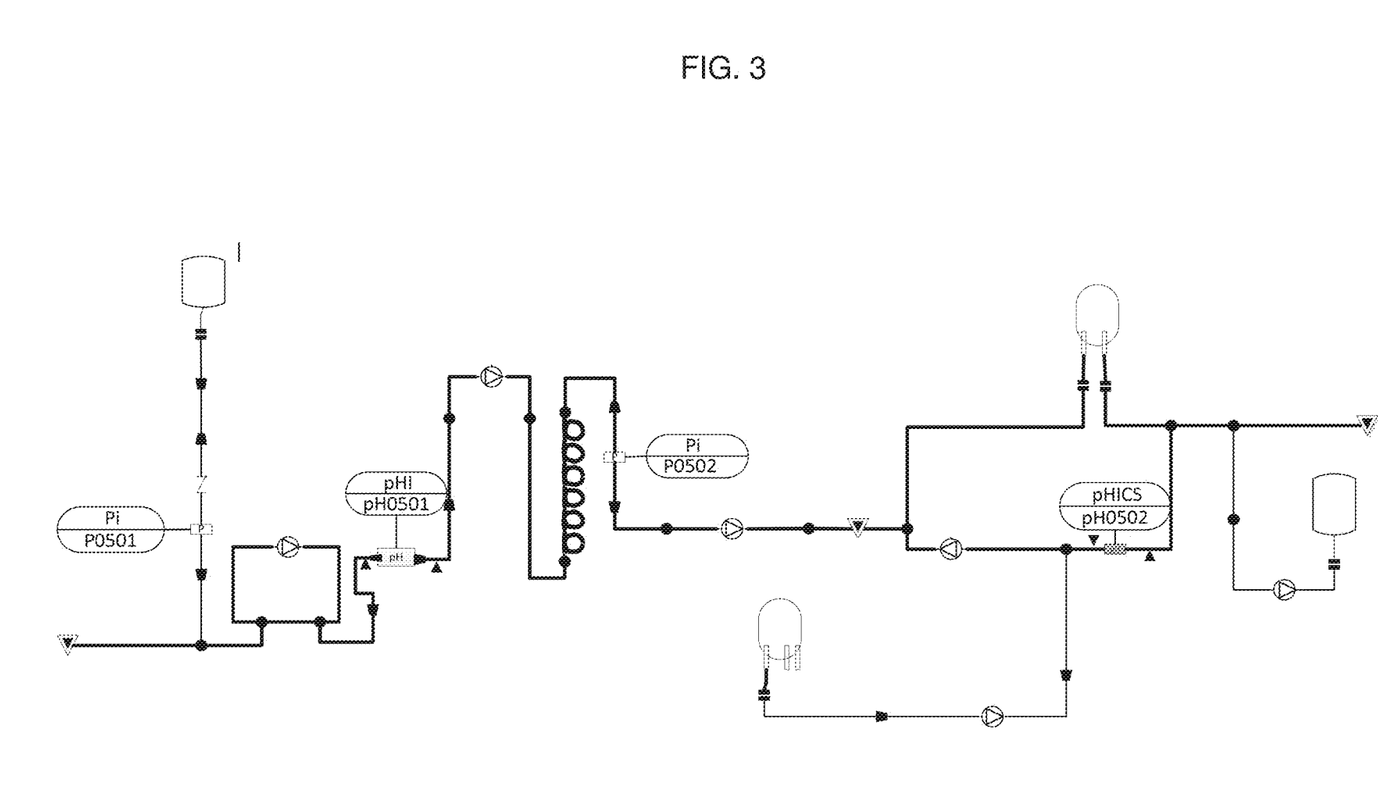
FIG. 3 shows exemplarily the two process steps of virus inactivation and neutralization—two units which are set up in a modular manner, with the pH probes pH0501 and pH0502 being autoclaved and the rest being gamma-irradiated. The pH probes pH0501 and pH0502 are then welded into an assembly. The bags are connected via aseptic GE ReadyMate® connectors. The connection to Prot-A and to the filtration unit is at first weldedshut and is then welded to the various units.

Line segments with pH probes, in this case pH0501 and pH0502, were autoclaved. pH probe segments were then welded into assemblies. As shown, bags were connected via aseptic GE ReadyMate® connectors. The connections to the Prot-A eluate line and the filtration module were firstly welded shut and were then welded to the various modules.

0.2 µm Filtration

As it was possible for proteins to precipitate after a pH shift, the precipitated protein were filtered off.

Chromatography (Intermediate and Polish)

The product of the above 0.2 µm filtration was purified via two chromatography steps by means of four sequentially (4-PCC) operated 2.5 ml Capto Adheres (2.5 ml GE) and then two alternatingly operated 20 ml anion exchangers (Pall Hypercel StarAX). In this purification, Prot-A leachables, DNA, HCP and aggregates were removed. The two chromatography steps were connected to one another via a gamma-irradiated bag (GE ReadyCircuit® 1 litre), in which conductivity was adjusted to 7.5 mS/cm by the supply of water in line with the requirements of the anion exchanger.

The entire flow path including the columns was sanitized or gamma-irradiated. The load per cycle was 50 column volumes per column. The buffers used were acetate buffers with differing molarity, pH and conductivities. All buffers were filtered into a gamma-irradiated bag using a gamma-irradiated or autoclaved 0.2 µm filter. The outlet tubing of the buffer bags was welded to the inlets of the BioSMB system. Said system had at each of its inlets a gamma-irradiated degassing membrane (Liquicell Micro Module, Membrana). Similarly, the product line of the above 0.2 µm filtration was welded to the inlet of the BioSMB system via such a degasser. All inlet streams were then degassed by means of a vacuum pump at 50 mbar. The waste stream was conducted into a gamma-irradiated 200 litre Sartorius Flexboy.

The Flexboy was exchanged by rewelding using a Sartorius welder.

The product stream was again collected in a gamma-irradiated product bag (GE ReadyCircuit 1 litre).

Prefiltration

From the product bag of the polishing chromatography, the product solution was firstly prefiltered using a 0.1 µm capsule (Sartopore2, MidiCap size 9, 0.2 m$^2$). The procedure and setup were similar to "B. Downstream DSP-1-i) Cell clarification".

Virus Filtration

The outlet line from the prefiltration was directly connected by welding via a peristaltic pump to the inlet of the virus filtration from "C. Downstream DSP-II". Otherwise, the setup and operation of the virus filtration from "C. Downstream DSP-II" were similar to "C. Downstream DSP-II-0.2 µm Filtration". However, the virus filter used was a Virosart CPV filter (MidiCap size 9, 0.2 m$^2$), which was rinsed and autoclaved according to the manufacturer's instructions. Again, the filters were welded into the assembly. The product stream was again pumped into a gamma-irradiated product bag (GE ReadyCircuit 1 litre).

Final Concentration and Rebuffering

The final concentration and rebuffering was set up similarly to the above "B. DSP-I-ii) Concentration and rebuffering" and differed only in that an autoclaved UV cell was integrated into the concentration loop for monitoring of the product concentration. The rebuffering was carried out similarly to the above "B. DSP-I-ii) Concentration and rebuffering", with a 50 mM phosphate buffer, pH 7.5 being used in this case. The product stream was again pumped into a gamma-irradiated product bag (GE ReadyCircuit 1 litre).

0.2 µm Filtration

The final filtration was carried out as described above in "B. DSP-1 i)" across gamma-irradiated Sartopore 2 capsules (Midicap size 7, 0.05 m$^2$) into a gamma-irradiated 5 litre GE ReadCircuit bag. When the fill level of the final bag was acceptable, said bag was welded off and a new bag was welded to the process.

A regularly performed run time of the process according to the invention, as described in Example 1, was 3 days with no microbial growth, with the chromatography columns being sanitized by 40% isopropanol+0.5 M NaOH. In the case of run times of over 3 days for the process according to the invention, the chromatography columns were gamma-irradiated.

The averaged flow rates and antibody concentrations of the positions shown in FIG. 1 are summarized in Table 1.

TABLE 1

|  | Process stream — | Volumetric flow rate ml min$^{-1}$ | Antibody concentration g l$^{-1}$ | Antibody flow rate g d$^{-1}$ |
|---|---|---|---|---|
| Upstream & Downstream I | 1 | 33.3 | 0.0 | 0.00 |
|  | 2 | 33.3 | 0.1 | 5.5 |
|  | 3 | 33.3 | 0.1 | 5.5 |
|  | 4 | 5.3 | 0.7 | 5.4 |
|  | 5 | 5.3 | 0.7 | 5.4 |
| Downstream II | 6 | 30 | 0.7 | 30.0 |
|  | 7 | 30 | 0.7 | 30.0 |
|  | 8 | 4.2 | 4.6 | 28.0 |
|  | 9 | 4.6 | 4.2 | 28.0 |
|  | 10 | 9.3 | 1.8 | 23.6 |
|  | 11 | 9.3 | 1.7 | 23.3 |

TABLE 1-continued

| Process stream — | Volumetric flow rate ml min$^{-1}$ | Antibody concentration g l$^{-1}$ | Antibody flow rate g d$^{-1}$ |
|---|---|---|---|
| 12 | 2.0 | 8.0 | 22.8 |
| 13 | 2.0 | 8.0 | 22.7 |

The work which led to this application was funded in accordance with the "Bio.NRW: MoBiDiK—Modulare Bioproduktion—Disposable and Kontinuierlich" [Bio.NRW: MoBiDiK—modular bioproduction—disposable and continuous] grant agreement as part of the European Regional Development Fund (ERDF).

The invention claimed is:

1. A method for continuous, microbe-reduced production and/or processing of a biopharmaceutical, biological macromolecular product from a heterogeneous cell culture-fluid mixture, comprising:
(a) providing a particle-free fluid from a heterogeneous cell culture-fluid mixture containing the product, in the form of a product stream, (b) at least one filtration, providing a filtrate, (c) at least two chromatography steps for purifying the product, (d) at least one virus depletion selected from the group consisting of pH adjustment by way of suitable acid, use of a solvent and detergent treatment, and by UV or thermal treatment, (e) at least one ultrafiltration and/or at least one diafiltration of the product stream of (b), (c) and/or (d),
wherein the at least two chromatography steps from (c) comprise a purification via at least two chromatography columns and/or membrane adsorbers and wherein
the method is carried out in a closed and modular manner and is adapted to allow for addition of materials from outside the closed and modular manner,
wherein the product is not exposed to a room environment, and
wherein all elements used in (a) to (e) that come into contact with the product are subjected to microbe reduction via a microbe-reduction method, the microbe-reduction method being selected from the group consisting of gamma irradiation, beta irradiation, autoclaving, ethylene oxide (ETO) treatment, ozone ($O_3$) treatment, hydrogen peroxide ($H_2O_2$) treatment and steam-in-place (SIP) treatment,
wherein at least one filtration step comprising at least one filter is carried out between a) to e) and/or thereafter,
and wherein the filter is automatically changed under microbe-reduced conditions, the automatic filter change comprising:
(i) switching of the flow path to a new filter in the event of exceeding of a threshold at a pressure sensor on the non-filtrate side with closing of the flow path, or in the event of exceeding of a maximum time of the used filter in the flow path, or in the event of exceeding of a maximum volume of filtrate through the used filter,
(ii) venting of the new filter via an air filter having a pore size of <=0.25 µm at the venting valve of the new filter,
(iii) detecting the completion of venting of the new filter on the non-filtrate side by means of the pressure sensor or a fill-level sensor or a balance or a liquid detector, (iv) opening the filtrate outlet and closing the flow path between the venting valve and the air filter by means of a valve, and
(v) exchanging the used filter for a new filter.

* * * * *